(12) United States Patent
Dalko et al.

(10) Patent No.: US 11,602,496 B2
(45) Date of Patent: Mar. 14, 2023

(54) USE OF GINGERONE OR DERIVATIVES THEREOF FOR REDUCING OR DELAYING THE SIGNS OF SKIN AGEING

(71) Applicant: L'OREAL, Paris (FR)

(72) Inventors: Maria Dalko, Versailles (FR); Sophie Saussay, Piailly (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/894,530

(22) Filed: Feb. 12, 2018

(65) Prior Publication Data

US 2018/0161257 A1 Jun. 14, 2018

Related U.S. Application Data

(63) Continuation of application No. 14/009,218, filed as application No. PCT/EP2012/055886 on Mar. 30, 2012, now abandoned.

(60) Provisional application No. 61/472,659, filed on Apr. 7, 2011.

(30) Foreign Application Priority Data

Apr. 1, 2011 (FR) ...................................... 1152803

(51) Int. Cl.
*A61K 8/35* (2006.01)
*A61Q 19/08* (2006.01)
*A61K 8/34* (2006.01)

(52) U.S. Cl.
CPC ................ *A61K 8/35* (2013.01); *A61K 8/347* (2013.01); *A61Q 19/08* (2013.01)

(58) Field of Classification Search
CPC ............................... A61K 8/347; A61Q 19/08
See application file for complete search history.

(56) References Cited

U.S. PATENT DOCUMENTS

| | | | |
|---|---|---|---|
| 5,747,049 A | 5/1998 | Tominaga | |
| 5,853,705 A * | 12/1998 | Nakayama | A61K 8/0212 424/59 |
| 8,765,101 B2 * | 7/2014 | Marion | A61Q 17/04 424/59 |
| 9,358,192 B2 * | 6/2016 | Marion | A61Q 17/04 |
| 2007/0071710 A1 * | 3/2007 | Maestro | A61K 8/97 424/74 |
| 2007/0259057 A1 | 11/2007 | Sugita et al. | |
| 2008/0025930 A1 * | 1/2008 | Corstjens | A61Q 19/08 424/59 |
| 2009/0149550 A1 | 6/2009 | Sugita et al. | |

FOREIGN PATENT DOCUMENTS

| | | | | |
|---|---|---|---|---|
| EP | 0 334 967 A1 | 10/1989 | | |
| EP | 1 800 651 A1 | 6/2007 | | |
| EP | 2 327 393 A2 | 6/2011 | | |
| JP | 8-225428 A | 9/1996 | | |
| JP | 8-268859 A | 10/1996 | | |
| JP | 9-30927 A | 2/1997 | | |
| JP | 2003206239 A * | 7/2003 | | |
| JP | 2003206239 A | 7/2003 | | |
| KR | 10-2004-0094506 A | 11/2004 | | |
| WO | WO-2006063056 A1 * | 6/2006 | | A61Q 17/00 |
| WO | WO-2009049172 A1 * | 4/2009 | | A61K 8/347 |
| WO | WO 2011/042358 A1 | 4/2011 | | |
| WO | WO-2011042358 A1 * | 4/2011 | | A61Q 17/04 |
| WO | WO 2011/063863 A2 | 6/2011 | | |
| WO | WO 2011/063864 A2 | 6/2011 | | |
| WO | WO 2011/063865 A2 | 6/2011 | | |

OTHER PUBLICATIONS

Jadhav (Journal of Food Engineering vol. 93 pp. 421-426 published 2009) (Year: 2009).*
Shin et al (J. Agric. Food Chem vol. 53 pp. 7617-7622, published 2005) (Year: 2005).*
Jadhav et al., (Journal of Food Engineering vol. 93, pp. 421-426 published 2009). (Year: 2009).*
Shin et al., (J. Agric. Food Chem vol. 53 pp. 7618-7622. Published 2005). (Year: 2005).*
Berlin (J Gen Chem of USSR vol. 19 pp. 1-19. Published 1949) (Year: 1949).*
Shin (Journal of Agricultural and Food Chemistry vol. 53, pp. 7617-7622. Published 2005) (Year: 2005).*
Halliwell (Annals of the Rheumatic Diseases vol. 54 pp. 505-510, published 1995 (Year: 1995).*
International Search Report dated Aug. 28, 2012 in PCT/EP2012/055886.
Gurdip Singh, et al., "Chemistry, antioxidant and antimicrobial investigations on essential oil and oleoresins of *Zingiber officinale*" Food and Chemical Toxicology, vol. 46, No. 10, XP025474571, Oct. 1, 2008, pp. 3295-3302.

(Continued)

*Primary Examiner* — Theodore R. Howell
*Assistant Examiner* — George W Kosturko
(74) *Attorney, Agent, or Firm* — Womble Bond Dickinson (US) LLP

(57) ABSTRACT

The present invention relates to the cosmetic use of at least one compound of general formula (I):

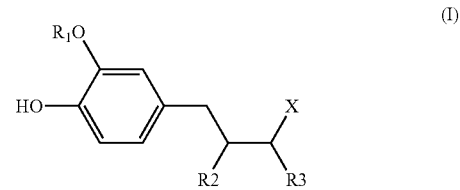

in which:
R$_1$ represents a methyl or ethyl radical;
R$_2$ represents a hydrogen atom or a methyl or ethyl radical;
R$_3$ represents a linear C$_1$-C$_6$ or branched C$_3$-C$_6$ alkyl radical, or a linear C$_2$-C$_6$ or branched C$_3$-C$_6$ alkenyl radical; and
X represents =O or —OH,
as an agent for reducing and/or delaying the signs of skin ageing.

18 Claims, No Drawings

(56) References Cited

OTHER PUBLICATIONS

Sandilands et al., (Journal of Cell Science vol. 122 1285-1294. Published 2009).
Chen, J.-C. et al., Journal of Agricultural and Food Chemistry vol. 55 pp. 8390-8397. Published 2007.
Everyday Health: The Aging Effect of UV Rays (published online Oct. 2009).
Rie Suzuki et al, "Reaction of Retinol with Peroxynitrite", Biosci, Biotechnol. Biochem, 71(10), 2596-2599, 2007.

* cited by examiner

USE OF GINGERONE OR DERIVATIVES THEREOF FOR REDUCING OR DELAYING THE SIGNS OF SKIN AGEING

CROSS-REFERENCE TO RELATED APPLICATIONS

This application is a Continuation of U.S. Ser. No. 14/009,218 filed Oct. 1, 2013, which is a National Stage of PCT/EP2012/055886, filed Mar. 30, 2012, and claims the benefit of U.S. Provisional Application No. 61/472,659, filed Apr. 7, 2011 and FR 11 52803, filed Apr. 1, 2011.

The present invention relates to the field of ageing and of the signs that are associated therewith, on the skin. It relates in particular to the adjustment of the equilibrium between the proliferation and the differentiation of the epidermal cells.

Women, or even men, currently have a tendency to want to look young for as long as possible and consequently seek to tone down the signs of skin ageing, which result in particular in wrinkles and fine lines, a thinning of the epidermis and/or a flaccid and withered skin appearance. In this regard, the advertising and fashion industries mention products for retaining radiant and wrinkle-free skin, signs of youthful skin, as long as possible, all the more so since physical appearance has an effect on the psyche and/or on morale.

The skin constitutes a physical barrier between the body and its surroundings. It is constituted of two tissues: the epidermis and the dermis.

The dermis provides the epidermis with a solid support. It is also its nourishing element. It is formed mainly from fibroblasts and an extracellular matrix, which is itself composed mainly of collagen, elastin and a substance known as ground substance, these components being synthesized by the fibroblast. Leukocytes, mast cells or else tissue macrophages are also found therein. It also contains blood vessels and nerve fibres.

The epidermis is a desquamating pluristratified epithelium that is 100 μm thick on average and is conventionally divided into a basal layer of keratinocytes that constitutes the germinal layer of the epidermis, a spinous layer constituted of several layers of polyhedral cells positioned on the germinal cells, a granular layer constituted of flattened cells containing distinct cytoplasmic inclusions, keratohyalin granules, and finally an upper layer known as the cornified layer (or stratum corneum), constituted of keratinocytes at the terminal stage of their differentiation, known as corneocytes. These are mummified anucleated cells which derive from keratinocytes. The stack of these corneocytes constitutes the cornified layer that is responsible, inter alia, for the barrier function of the epidermis, i.e. it constitutes a barrier against external attacks, especially chemical, mechanical or infectious attacks and it also makes it possible to protect the body from water loss.

Epidermal differentiation follows a process of continuous and oriented maturation in which the basal keratinocytes transform while migrating so as to result in the formation of corneocytes, dead cells that are completely keratinized. This differentiation is the result of perfectly coordinated phenomena which will result in the thickness of the epidermis being kept constant and thus ensure the homeostasis of the epidermis. This goes through a regulation of the number of cells that enter into the differentiation process and of the number of cells that desquamate. In the course of the normal desquamation process, only the most superficial corneocytes detach from the surface of the epidermis.

Keratins are insoluble proteins produced by the epithelial cells in the form of structurally well organized filaments. These proteins are the main marker of differentiation since throughout epidermal differentiation, various types of keratin will be more or less expressed by the keratinocytes.

Other proteins, associated with keratins, play very important roles in the skin. Filaggrin (or filagrin), a protein present in keratohyalin granules, is produced during the final stages of the differentiation of the epidermis. It is especially involved in the maturation process of the cornified layer by enabling type I and type II keratins to be arranged into coils. This protein thus enables the formation of the cytoplasmic matrix of the surface corneocytes which in particular gives the skin its normal thickness, its smooth appearance and its light-reflecting properties. Furthermore, via its degradation within corneocytes, filaggrin provides water-soluble substances having a high osmotic power (natural moisturizing factors or NMFs) that enable a good hydration of the cornified layer of the skin to be maintained and thus avoid the feelings of "dry skin". Filaggrin therefore enables the barrier function of the epidermis to be maintained and makes it possible to avoid drying out the skin.

In the course of chronobiological ageing, the thickness of the epidermis is reduced, maturation of the keratinocytes is imperfect and keratinization no longer leads to an even and homogeneous cornified layer being created. It is also known that prolonged and/or repeated exposures to the sun lead to quite similar results on the epidermis. This is photoinduced ageing. It is also known that, at the menopause, skin ageing accelerates, the thickness of the epidermis decreases, women complain of their skin tightening and that it takes on the look of "dry skin", or even of the appearance of xerosis.

Surprisingly, the inventors have demonstrated that gingerone and some of the derivatives thereof increased the expression of filaggrin in the keratinocytes. As filaggrin is a marker of the differentiation of keratinocytes, gingerone and some of the derivatives thereof therefore have an effect of stimulating the differentiation of these cells and thus the maturation of the cornified layer. They thus enable the skin to retain or regain a normal thickness, to also have a smooth appearance, i.e. without, or with fewer, wrinkles and fine lines than before their use and a more radiant, less dull complexion.

Furthermore, since filaggrin is involved in the skin hydration process, by increasing the expression of this protein in keratinocytes, these compounds enable the skin to fully carry out its barrier function while avoiding, in particular, the drying out thereof. They therefore make it possible to reestablish or maintain good hydration of the skin.

These compounds therefore prove particularly advantageous for combating the appearance of the signs of skin ageing and for combating the drying out of the skin, whether or not this is linked to the ageing thereof.

Gingerone (INCI name: Zingerone), is a phenolic compound from the vanilloid family. Its formula and those of several of its derivatives are given below. Ginger (*Zingiber officinale*), mango, cranberry or raspberry may be natural sources of gingerone. Ginger, and in particular ginger oleoresin, is however the main source thereof. This molecule is to a large extent responsible for the hot flavour of ginger.

Gingerone has already been cited among the ingredients of topical anti-ageing care compositions but it was used as a blood circulation "accelerator" (JP 2004323401, JP 2005066831) or as a hyperemizing agent (EP 1 938 789) or as an antioxidant (EP 1 932 514) or as a caustic, bitter or acid substance (JP 2004210656).

To the knowledge of the inventors, gingerone and some of the derivatives thereof have never been described as being pro-differentiating for keratinocytes and as being able to be used specifically for treating or delaying the appearance of the signs of skin ageing.

One subject of the present invention is thus the use of at least one compound of general formula (I):

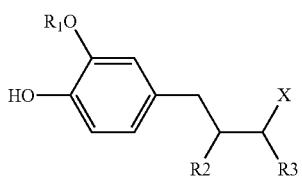

in which:
- $R_1$ represents a methyl or ethyl radical;
- $R_2$ represents a hydrogen atom or a methyl or ethyl radical;
- $R_3$ represents a linear $C_1$-$C_6$ or branched $C_3$-$C_6$ alkyl radical, or else a linear $C_2$-$C_6$ or branched $C_3$-$C_6$ alkenyl radical; and
- X represents =O or —OH, as an agent for reducing and/or delaying the signs of skin ageing.

Preferably, these compounds are of general formula (I) in which:
- $R_1$ represents a methyl or ethyl radical;
- $R_2$ represents a hydrogen atom or a methyl or ethyl radical;
- $R_3$ represents a $C_1$-$C_6$ linear alkyl; and
- X represents =O or —OH.

In particular, use will be made of compounds of general formula (I) in which:
- $R_1$ represents a methyl or ethyl radical;
- $R_2$ represents a hydrogen atom or a methyl or ethyl radical;
- $R_3$ represents a $C_1$-$C_6$ linear alkyl; and
- X represents =O.

According to the present invention, the compound of general formula (I) mentioned above will preferably be chosen, alone or as a mixture, from the following compounds:

| Number and name of the compound | Formula of the compound |
|---|---|
| Compound 1: Gingerone or Zingerone or vanillylacetone CAS number: 122-48-5 | |
| Compound 2: 4-(3-ethoxy-4-hydroxyphenyl)-2-butanone (7Ci) or ethyl gingerone CAS number: 569646-79-3 | |
| Compound 3: 4-(3-ethoxy-4-hydroxyphenyl)-2-butanol | |
| Compound 4: 1-paradol CAS number: 53171-99-6 | |
| Compound 5: 4-(3-methoxy-4-hydroxyphenyl)-3-methylbutane-2-one CAS number: 83092-97-1 | |
| Compound 6: 3-paradol CAS number: 53172-01-3 | |
| Compound 7: 1-(4-hydroxy-3-methoxyphenyl) nonan-3-one CAS number: 53172-03-5 | |

The preferred compound will be chosen from gingerone (or zingerone) or ethyl gingerone. The gingerone may be, for example, supplied by the company Aldrich. Most preferred is ethyl gingerone.

Compounds 2 and 7 may be, for example, supplied by the company SinoChemExper.

The compounds of general formula (I), as targeted above, could be used in the form of a more or less purified molecule of natural or synthetic origin. They will preferably be of natural origin. In particular, some of these compounds could be provided in the form of plant extracts containing them, and especially in the form of an extract of ginger, of mango, of cranberry and/or of raspberry.

Such compounds may be synthesized via synthesis pathways known in the prior art. They may in particular be prepared from commercial vanillin or ethyl vanillin. Gingerone, for example, could be obtained via the condensation of vanillin by acetone, followed by a hydrogenation.

The expression "cutaneous signs of ageing" is understood to mean any modification in the external appearance of the skin due to ageing, whether chronobiological and/or photoinduced, such as, for example, wrinkles and fine lines, withered skin, flaccid skin, slack skin, thinned skin, dry skin, dull skin that lacks radiance, heterogeneity of the complexion and of the surface of the skin. The signs of chronobiological or chronological ageing (also known as chronoageing) correspond to internal degradations of the skin due to the intrinsic ageing of the individuals. The signs of photoinduced ageing (or photoageing) correspond to internal degradations of the skin following exposure to ultraviolet radiation.

The term "skin" is understood to mean, for the purposes of the invention, the whole of the body covering, and in particular the skin, mucous membranes and scalp.

The reduction of the signs of skin ageing and/or the delaying of their appearance, via the use of the compounds according to the present invention, takes place in particular owing to the increase or improvement in the differentiation of the epidermal cells and/or the increase or stimulation in particular of the expression of filaggrin in the epidermal keratinocytes.

Preferably, the compositions used according to the invention are cosmetic compositions, i.e. they are intended to improve the aesthetic appearance of the individual.

The use according to the present invention is especially effective for combating the signs, in particular aesthetic signs, of chronobiological and/or photoinduced ageing of the epidermis. Through the present invention, combating the signs of chronobiological ageing of the skin will preferably be targeted.

The present invention is thus effective in any person regardless of their age. When combating the signs of chronobiological ageing, the individuals preferably targeted will be individuals of more than 30 years old, preferably more than 40 years old.

The signs of skin ageing are preferably chosen from the appearance of wrinkles and fine lines and/or the weakening and/or the slackening and/or the withering and/or the thinning and/or the dryness and/or the dull and/or non-radiant appearance and/or the complexion and/or the heterogeneous surface of the skin.

Through the present invention, skin having a more youthful appearance and better hydrated skin are therefore obtained.

The compound of general formula (I) as targeted above is present, in a composition comprising a physiologically acceptable medium, in a content between 0.1% and 10% by weight relative to the total weight of said composition.

A "physiologically acceptable medium" is, according to the invention, a cosmetically acceptable medium that is compatible with the skin, the mucous membranes, the nails and/or the hair.

The expression "cosmetically acceptable medium" is understood to mean a medium that has no unpleasant appearance, and that does not cause the user any unacceptable stinging, tautness or redness.

The physiologically acceptable medium will be adapted to the nature of the support onto which the composition is to be applied, and also to the form in which the composition is intended to be packaged, in particular solid or fluid at room temperature and atmospheric pressure.

The composition is preferably suitable for topical application.

For an administration via topical application to the skin and/or the mucous membranes, the composition according to the invention of course comprises a cosmetically acceptable support, i.e. a support that is compatible with the skin, the mucous membranes, the nails, the hair, and may be in any galenic form normally used for a topical application, in particular in the form of an aqueous, aqueous-alcoholic or oily solution, an oil-in-water or water-in-oil or multiple emulsion, an aqueous or oily gel, a liquid, pasty or solid anhydrous product, a suspension or a dispersion; for example a dispersion of oil in an aqueous phase using spherules, it being possible for these spherules to be polymeric nanoparticles, such as nanospheres and nanocapsules, or better still lipid vesicles of ionic and/or nonionic type.

This composition may be more or less fluid and may have the appearance of a white or coloured cream, an ointment, a milk, a lotion, a serum, a paste or a foam. It can optionally be applied to the skin in aerosol form. It can also be in solid form, for example in the form of a stick. It can be used as a care product or as a cleansing product or as a makeup product.

In a known manner, the composition of the invention may contain adjuvants that are common in the cosmetic and dermatological fields, such as hydrophilic or lipophilic gelling agents, hydrophilic or lipophilic active agents, preserving agents, antioxidants, solvents, fragrances, fillers, screening agents, pigments, chelating agents, odour absorbers and colorants. The amounts of these various adjuvants are those conventionally used in the fields under consideration, for example from 0.01% to 20% of the total weight of the composition. Depending on their nature, these adjuvants may be introduced into the fatty phase, into the aqueous phase, into the lipid vesicles and/or into the nanoparticles.

When the composition of the invention is an emulsion, the proportion of the fatty phase may range from 5% to 80% by weight and preferably from 5% to 50% of the total weight of the composition. The oils, emulsifiers and coemulsifiers used in the composition in emulsion form are chosen from those conventionally used in the field under consideration. The emulsifier and the coemulsifier are present in the composition in a proportion ranging from 0.3% to 30% by weight and preferably from 0.5% to 20% of the total weight of the composition.

As oils that can be used in the invention, mention may be made of mineral oils, oils of plant origin (apricot oil, sunflower oil), oils of animal origin, synthetic oils, silicone-based oils and fluorinated oils (perfluoropolyethers). As fatty substances, use may also be made of fatty alcohols (cetyl alcohol), fatty acids and waxes (beeswax).

As emulsifiers and coemulsifiers that can be used in the invention, mention may for example be made of polyethylene glycol fatty acid esters such as PEG-40 stearate and PEG-100 stearate, and polyol fatty acid esters such as glyceryl stearate and sorbitan tristearate.

As hydrophilic gelling agents, mention may particularly be made of carboxyvinyl polymers (carbomer), acrylic copolymers such as acrylate/alkyl acrylate copolymers, polyacrylamides, polysaccharides, natural gums and clays, and, as lipophilic gelling agents, mention may be made of modified clays such as bentones, metal salts of fatty acids, hydrophobic silica and polyethylenes.

According to one advantageous embodiment, the compositions according to the invention will contain at least one other active agent chosen from anti-UV screening agents, moisturizers, depigmenting agents, anti-glycation agents, NO-synthase inhibitors, agents for stimulating the synthesis of dermal or epidermal macromolecules and/or for preventing their degradation, agents for stimulating fibroblast or keratinocyte proliferation, myorelaxants or dermo-decontracting agents, tensioning agents, agents for combating pollution or free-radical scavengers, calmatives and active agents that act on the energy metabolism of cells.

The amount of these additional active agents could vary to a large extent and will be for example from $10^{-6}\%$ to 20% by weight, especially from 0.001% to 10% by weight relative to the total weight of the composition.

The agents for stimulating fibroblast proliferation that may be used in the composition according to the invention may be chosen, for example, from plant proteins or polypeptides, extracted especially from soybean (for example a soybean extract sold by the company LSN under the name Eleseryl SH-VEG 8® or sold by the company Silab under the trade name Raffermine®); and plant hormones such as gibberellins and cytokinins.

The agents for stimulating keratinocyte proliferation that can be used in the composition according to the invention especially comprise retinoids such as retinol and esters thereof, including retinyl palmitate; adenosine, cinnamic acid and derivatives thereof, lycopene and derivatives thereof; phloroglucinol; the walnut meal extracts sold by the company Gattefossé; and the extracts of *Solanum tuberosum* sold by the company Sederma.

Preferably, for the implementation of the invention, the compound of general formula (I) as described above, and/or the composition containing it, will be applied to the part of the skin to be treated, in particular to the face, the neck or the hands, daily or several times daily; the application will be repeated every day for a variable period depending on the effects desired, generally from 3 to 6 weeks, but which could be extended or carried out continuously.

The compound of general formula (I) as described above or the composition containing it will preferably be applied to the areas of skin affected by the signs of ageing that it is desired to combat.

For an oral administration, the composition of the invention may be in any suitable form, particularly in the form of a solution to be taken orally, a tablet, a gel capsule, a capsule or alternatively a nutritional food or a nutritional supplement.

Said composition additionally comprises at least one appropriate excipient suitable for oral administration.

In the case of active agents or of compositions according to the invention being taken orally, the oral administration may be daily or several times daily, for example morning and evening. It could be continued for several weeks and/or several months, depending on the effects desired.

The examples given below are presented as non-limiting illustrations of the invention.

EXAMPLES

1. Method of Preparing a Compound According to the Invention

The method of preparing these compounds of general formula (I) may be, for example, the following:

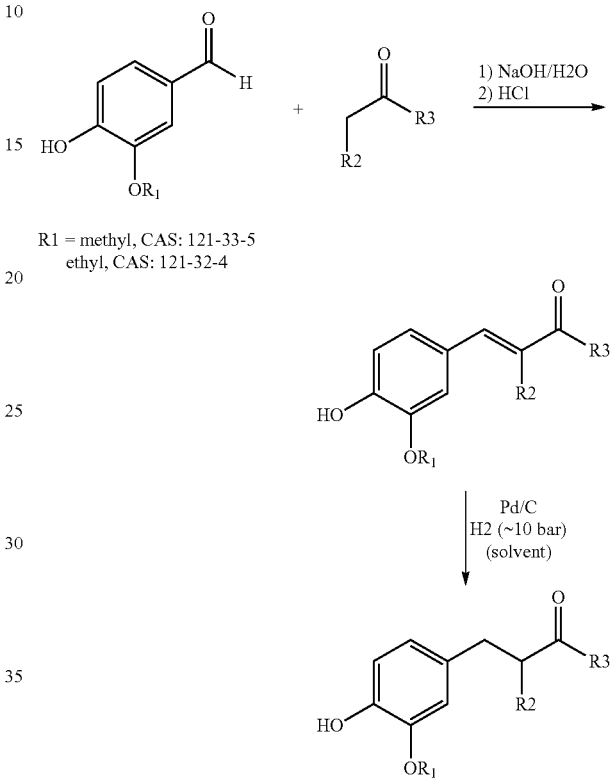

R1 = methyl, CAS: 121-33-5
ethyl, CAS: 121-32-4

The method of preparing compound 3 comprises a supplementary reduction step:

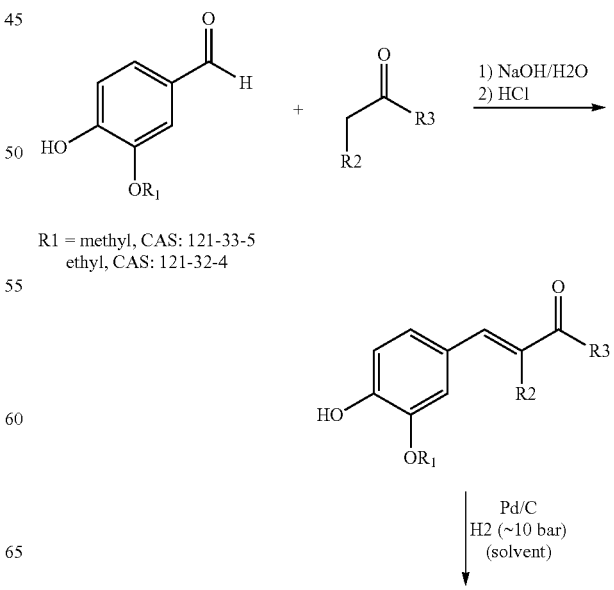

R1 = methyl, CAS: 121-33-5
ethyl, CAS: 121-32-4

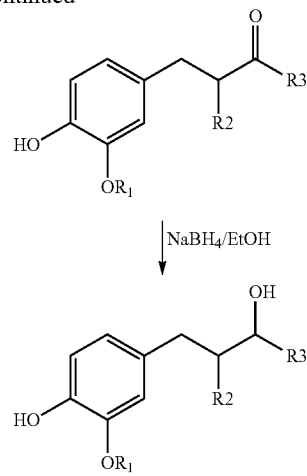

The compounds according to the invention are prepared here either from commercial vanillin (CAS: 121-33-5), or from commercial ethyl vanillin (CAS: 121-32-4).

2. Demonstration of the Activity of a Compound According to the Invention

The in vitro effect of gingerone (compound 1, the chemical formula of which is given above) on keratinocyte differentiation is studied. The expression and the location of the marker of filaggrin differentiation are especially studied in keratinocytes in culture which thus makes it possible to evaluate the capacity of this compound to increase the differentiation of these cells.

Procedure:

Normal human keratinocytes (NHEKs) were cultured at 37° C. and 5% $CO_2$ for 24 h in a complete SFM medium until moderate confluence was obtained. A complete SFM medium is an SFM culture medium supplemented with pituitary extract (25 µg/ml), EGF (0.25 ng/ml) and gentamicin (25 µg/ml).

At the end of the incubation, the medium was withdrawn and replaced with culture medium that did or did not contain various concentrations of the test product or reference molecules. Calcium chloride and retinoic acid, which are known respectively as a stimulator and as an inhibitor of the keratinocyte differentiation, were used as reference molecules for this test. The keratinocytes were then incubated for 144 hours. The treatments were carried out in triplicate (n=3).

At the end of the incubation, the culture medium was removed and the cells were rinced, fixed, permeabilized then labelled with the primary antibody targeted against the filaggrin protein of interest (in situ immunolabelling). This antibody was then revealed by a secondary antibody coupled to a fluorochrome (GAM-Alexa 488). At the same time, the nuclei of the cells were stained with Hoechst 33258 (bis-benzimide).

Image acquisition was carried out using an INCell Analyzer™1000 machine. The labels were quantified by measuring the fluorescence intensity of the proteins relative to the number of nuclei identified by the Hoechst product.

Results

The results are given in Table 1 below:

TABLE 1

| Treatment | | % relative to the control |
|---|---|---|
| Control complete SFM medium | | 100 |
| $CaCl_2$ | 1.5 mM | 158** |
| Retinoic acid | $10^{-7}$ M | 3** |
| Gingerone | 2 µg/ml | 133* |
| | 20 µg/ml | 151* |

Significant difference relative to the control medium (*$p < 0.05$ and **$p < 0.01$).

Under the experimental conditions of this study, the treatment with calcium chloride, pro-differentiating reference molecule, substantially increases the expression of filaggrin by the keratinocytes (+58% relative to the control).

Under the experimental conditions of this study, the treatment with retinoic acid, anti-differentiating reference molecule, substantially decreases the expression of filaggrin by the keratinocytes (−97% relative to the control).

The treatment with gingerone at 2 µg/ml and 20 µg/ml significantly and dose-dependently stimulates the expression of filaggrin (+33% and +51% respectively relative to the control) by the keratinocytes.

Conclusion

Gingerone significantly and dose-dependently increases the expression of the filaggrin protein in normal human epidermal keratinocytes.

The results obtained thus translate into an increase in epidermal differentiation. Gingerone therefore has a pro-differentiating effect on normal human keratinocytes and therefore can thus reduce and/or delay the signs of skin ageing.

3. Composition Examples 3.1. Lotion

A lotion is prepared, comprising (% by weight):

| | |
|---|---|
| compound tested in Example 1 (gingerone) | 0.75% |
| glycerol | 2% |
| ethyl alcohol | 20% |
| demineralized water | qs 100% |

The composition according to the invention applied daily to the face makes it possible to combat the signs of skin ageing.

3.2. Facial Gel

A facial gel is prepared, comprising (% by weight):

| | |
|---|---|
| glyceryl polyacrylate (Norgel) | 30% |
| polyacrylamide/C13-14 isoparaffin/laureth-7 (Sepigel 305) | 2% |
| silicone oil | 10% |
| compound 1 (gingerone) | 5% |
| water | qs 100% |

The composition according to the invention applied daily to the face makes it possible to combat the signs of skin ageing.

The invention claimed is:

1. A method for treating appearance of wrinkles, appearance of fine lines, thinning of the skin, dryness of the skin, or any combination thereof of skin on a subject having skin including appearance of wrinkles, appearance of fine lines, thinning of the skin, dryness of the skin, or any combination thereof, comprising:
applying to the appearance of wrinkles, appearance of fine lines, thinning of the skin, dryness of the skin, or any combination thereof, a compound of general formula (I) in an amount sufficient to treat the appearance of wrinkles, appearance of fine lines, thinning of the skin, dryness of the skin, or any combination thereof and in an amount sufficient to stimulate filaggrin protein expression in a human epidermal keratinocyte:

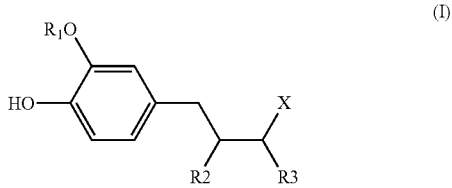

(I)

wherein:
$R_1$ is an ethyl radical;
$R_2$ is a hydrogen atom, a methyl radical or an ethyl radical;
$R_3$ is a linear $C_1$-$C_6$ alkyl radical, a branched $C_{3-6}$ alkyl radical, a linear $C_2$-$C_6$ alkenyl radical, or a branched $C_3$-$C_6$ alkenyl radical; and
X is =O or —OH.

2. The method according to claim 1, wherein $R_3$ is a $C_1$-$C_6$ linear alkyl.

3. The method according to claim 1, wherein the compound of general formula (I), alone or as a mixture, is at least one selected from the group consisting of:

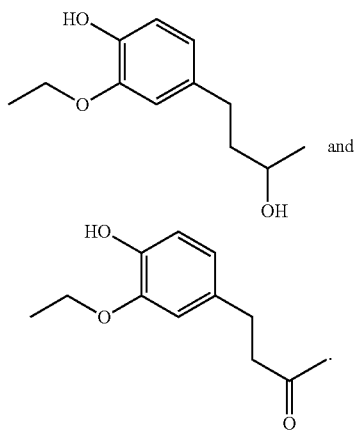

4. The method according to claim 1, wherein the compound of general formula (I) is ethyl gingerone.

5. The method according to claim 1, wherein the method comprises applying to the appearance of wrinkles a compound of general formula (I) in an amount sufficient to treat the appearance of wrinkles.

6. The method according to claim 1, wherein the compound of general formula (I) is present m a composition comprising a physiologically acceptable medium, wherein the compound of general formula (I) is present in the composition in a content between 0.1% and 10% by weight relative to a total weight of the composition.

7. The method according to claim 1, wherein the compound is applied in a cosmetic composition comprising the compound of general formula (I) in an amount of 0.1% to 10% by weight relative to a total weight of the cosmetic composition.

8. The method according to claim 7, wherein the cosmetic composition is a lotion.

9. The method according to claim 7, wherein the cosmetic composition is a gel.

10. A method for treating appearance of wrinkles, appearance of fine lines, or any combination thereof of skin on a subject having skin including appearance of wrinkles, appearance of fine lines; or any combination thereof comprising:
applying to the appearance of wrinkles, appearance of fine lines, or any combination thereof, a compound of general formula (I) in an amount sufficient to treat the appearance of wrinkles, appearance of fine lines, or any combination thereof and in an amount sufficient to stimulate filaggrin protein expression in a human epidermal keratinocyte:

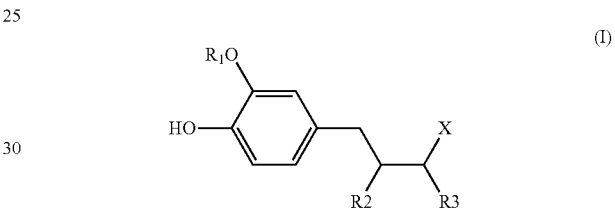

(I)

wherein:
$R_1$ is an ethyl radical;
$R_2$ is a hydrogen atom or a methyl or ethyl radical:
$R_2$ is a hydrogen atom, a methyl radical or an ethyl radical;
$R_3$ is a linear $C_1$-$C_6$ alkyl radical, a branched $C_3$-$C_6$ alkyl radical, a linear $C_2$-$C_6$ alkenyl radical, or a branched $C_3$-$C_6$ alkenyl radical; and
X is =O or —OH.

11. The method according to claim 10, wherein $R_3$ is a $C_1$-$C_6$ linear alkyl.

12. The method according to claim 10, wherein the compound of general formula (I), alone or as a mixture, is at least one selected from the group consisting of:

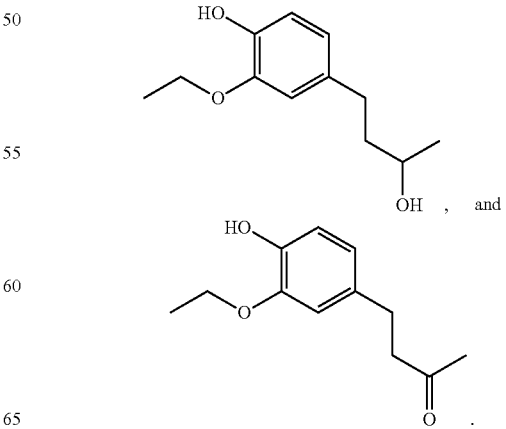

13. The method according to claim 10, wherein the compound of general formula (I) is ethyl gingerone.

14. The method according to claim 1, comprising treating signs of chronobiological ageing in a subject suffering from internal degradations of the skin due to intrinsic ageing of the individual.

15. The method according to claim 1, wherein the method comprises applying to the appearance of fine lines a compound of general formula (I) in an amount sufficient to treat the appearance of fine lines.

16. The method according to claim 1, wherein the method comprises applying to the thinning of the skin a compound of general formula (I) in an amount sufficient to treat the thinning of the skin.

17. The method according to claim 1, wherein the method comprises applying to the dryness of the skin a compound of general formula (I) in an amount sufficient to treat the dryness of the skin.

18. The method according to claim 6, wherein the composition does not contain anti-UV screening agents.

* * * * *